United States Patent [19]
Schlosser et al.

[11] Patent Number: 5,425,779
[45] Date of Patent: Jun. 20, 1995

[54] PROSTHETIC IMPLANT FOR JOINT STRUCTURES

[75] Inventors: Marc H. Schlosser, Austin; Richard J. Severson, Gonzales, both of Tex.; Gregory S. Musler, Glendale Heights, Ill.

[73] Assignee: U.S. Medical Products, Inc., Austin, Tex.

[21] Appl. No.: 203,860

[22] Filed: Mar. 1, 1994

Related U.S. Application Data

[63] Continuation of Ser. No. 926,043, Aug. 5, 1992, abandoned.

[51] Int. Cl.⁶ .................................. A61F 2/34
[52] U.S. Cl. .................................... 623/23
[58] Field of Search .................. 623/22, 23, 18

[56] References Cited

U.S. PATENT DOCUMENTS

| | | | |
|---|---|---|---|
| 3,584,318 | 1/1966 | Scales et al. | 623/18 |
| 3,723,995 | 4/1973 | Baumann | 623/22 |
| 3,813,699 | 6/1974 | Giliberty | |
| 3,863,273 | 2/1975 | Averill | |
| 4,172,296 | 10/1979 | D'Errico | 623/22 |
| 4,241,463 | 12/1980 | Khovaylo | 623/23 |
| 4,408,360 | 10/1983 | Keller | 623/23 |
| 4,714,477 | 12/1987 | Fichera et al. | 623/18 |
| 4,718,911 | 1/1988 | Kenna | 623/22 |
| 4,770,659 | 9/1988 | Kendall | 623/22 |
| 4,770,661 | 9/1988 | Oh | 623/23 |
| 4,798,610 | 1/1989 | Averill et al. | 623/22 |
| 4,813,961 | 3/1989 | Sostegni | 623/18 |
| 4,842,605 | 6/1989 | Sonnerat et al. | 623/18 |
| 4,871,368 | 10/1989 | Wagner | 623/18 |
| 4,908,033 | 3/1990 | Frey et al. | 623/22 |
| 4,919,674 | 4/1990 | Schelhas | 623/22 |
| 4,936,855 | 6/1990 | Sherman | 623/18 |
| 4,978,356 | 12/1990 | Noiles | 623/18 |
| 5,019,105 | 5/1991 | Wiley | 623/22 |
| 5,062,853 | 11/1991 | Forte | 623/22 |
| 5,156,626 | 10/1992 | Broderick et al. | 623/22 |
| 5,222,984 | 6/1993 | Forte | 623/18 X |

Primary Examiner—David Isabella
Attorney, Agent, or Firm—Shaffer & Culbertson

[57] ABSTRACT

A prosthetic implant for joint structures includes a shell, a head adapted to be secured to a bone leading to the joint structure in which the implant is to be used, an insert member adapted to be received in the shell and also adapted to receive the head, and a locking arrangement associated with the shell. The locking arrangement is adapted for releasably locking the insert member and head received therein in a receptacle in the shell. The locking arrangement preferably includes a ring of resilient material having an opening along part of its circumference for enabling the ring to resiliently expand and collapse. The ring is received in a groove inside the shell receptacle. As the insert member and head received therein are inserted into the shell, the ring expands into the groove allowing the insert member to pass. Once the insert member is fully received in the shell the ring snaps back to contact the insert member and retain it in the shell.

12 Claims, 2 Drawing Sheets

PROSTHETIC IMPLANT FOR JOINT STRUCTURES

This application is a continuation of application Ser. No. 07/926,043 filed Aug. 5, 1992 now abandoned.

BACKGROUND OF THE INVENTION

This invention relates to prosthetic implants for joint structures and particularly to a prosthetic implant structure and assembly method for arthroplasty involving ball and socket type joints.

Arthroplasty or joint replacement for ball and socket type joints includes providing an implant to replace the natural anatomic ball or head of the joint. Prosthetic implants for ball and socket type joints are classified as either unipolar or bipolar. A unipolar implant includes simply a head adapted to replace the ball structure of the natural joint and to articulate with the anatomic socket structure. Bipolar implants provide for articulation within the implant itself in addition to articulation with the anatomic socket structure. The added articulation within the implant structure reduces wear on the natural socket structure and provides better range of motion and freedom of movement in the joint.

Bipolar implants for ball and socket type joint structures such as the hip joint, for example, include a head or ball, a shell adapted to be received in the anatomic socket structure, and a receptacle in the shell. An insert member is commonly received in the shell receptacle and the implant head is adapted to be received directly in the insert member. In the case of a hip joint bipolar prosthesis, the implant head is adapted to be attached to the top of the femur after the natural femur head is resected. The implant head articulates with the insert in the shell and the shell articulates with the anatomic socket or acetabulum.

The manner in which the several components of a bipolar prosthetic implant are assembled is critical to the functioning of the implant. The implant head should be easily removable from the insert member and shell yet must be retained in the shell securely with minimal play so that the implant head freely articulates in the insert. To enhance the flexibility of the surgical implantation procedure, the implant should also be adapted for relatively quick assembly and disassembly with a minimum of small parts.

Prior prosthetic implants for ball and socket type joints fail to meet one or more of these requirements. For example, U.S. Pat. No. 3,863,473 to AVERILL discloses a prosthetic hip joint implant that uses a tab formed on the insert member and a cooperating groove on the inner surface of the shell to retain the insert member in the shell. This tab arrangement, however, requires that the tab deflect inwardly as the insert member is placed in the shell. When the tab snaps outwardly in the groove formed in the shell, the arm on which the tab is formed also moves outwardly and leaves excessive play between the head and the insert member.

The implant structure shown in U.S. Pat. No. 4,718,918 to KENNA retains the insert member in the shell with a lip formed on the inside surface of the shell and a cooperating groove formed on the outside surface of the insert. This locking or retaining arrangement results in either play between the insert member and the head received therein or play between the insert member and the shell. The retaining arrangement also makes it difficult to remove the insert member once it is connected with the shell.

Another type of prosthetic hip joint implant is shown in U.S. Pat. No. 4,241,463 to KHOVAYLO. This patent is directed to a prosthetic implant that retains the insert member in the shell with a rigid lip on the inside of the shell and an groove formed in the insert similarly to the KENNA patent. However, KHOVAYLO uses a retaining slip ring within the insert member itself to retain the head within the insert member. The space required for the ring in the insert member greatly reduces the bearing surface available for the head, and results in some degree of play between the insert member and the head.

SUMMARY OF THE INVENTION

It is an object of the invention to provide a prosthetic implant for joint structures that overcomes the above-described problems and others associated with prior implants. Another object of the invention to provide a method for assembling a prosthetic ball and socket type implant to overcome the above-described problems.

In order to accomplish these objects, a prosthetic implant embodying the principles of the invention includes a unique locking arrangement for locking the elements of a bipolar ball and socket type prosthetic implant together. The implant includes a shell, a head, and an insert member. The head is adapted to be received in a head receptacle formed in the insert member and the insert member is adapted to be received with the head therein in an insert receptacle formed in the shell. The locking arrangement includes locking means for releasably but securely locking the insert member in the shell while minimizing play between the insert member and inserted head and providing maximum bearing surface area for the head.

The locking means preferably includes a member that is adapted to extend into the insert receptacle in the shell in a locked position and to retract from the shell insert receptacle sufficiently to allow the insert member to be inserted into the insert receptacle. Once the insert member is received in the shell insert receptacle in a fully received position, the locking means is adapted to extend again into the insert receptacle to catch on a portion of the insert member and prevent the insert member from being removed from its fully received position in the shell insert receptacle.

In the preferred form of the invention the locking means comprises a locking ring mounted in an annular groove formed in the shell insert receptacle. The locking ring is made of a resilient material and includes an opening or split along part of its circumference so that it may be collapsed and placed in the annular groove. The resiliency of the locking ring material also enables the ring to retract as the insert member is inserted into the insert receptacle, and then spring back to retain the insert member in place. Also, a beveled edge is preferably formed on the inside edge of the locking ring. This beveled inside edge enables the ring to be expanded with a tool inserted into an annular space between the shell and the insert member so that the insert member may be easily removed from the shell.

According to the method of the invention, the head is first positioned within the head receptacle in the insert member. The opening to the head receptacle in the insert member preferably includes resilient means for expanding to receive the commonly spherically-shaped head and then spring back to retain the head in the insert member. With the head received in the insert member and the locking ring received in the annular groove of the shell, the method continues with the step of inserting the insert member into the shell insert receptacle. In the preferred form of the invention, contact between the insert member and the locking ring causes the ring to expand and retract from the insert receptacle to allow the insert member to pass. Finally, when the insert member reaches the fully received position in the shell, the locking ring resiliently springs back into the insert receptacle to catch on a step or other feature formed on the insert member to retain the insert member in the fully received position.

The prosthetic implant locking arrangement and component assembly method according to the invention provides several important advantages. First, the locking means does not require that a part of the insert member move outwardly once inserted into the shell to contact and catch on a portion of the shell. Thus the present invention avoids the play between the head and insert member that accompanies any outward movement by the insert member after or as it is inserted into a shell. The locking arrangement also allows close tolerance between the insert member and the shell and avoids play there between. The present locking arrangement additionally enables the insert member to provide the maximum bearing surface area for the head. Furthermore, since the locking ring can be manually collapsed, the insert member may be removed from the shell without having to exert a substantial pulling force on the shell.

These and other objects, advantages, and features of the invention will be apparent from the following description of the preferred embodiments, considered along with the accompanying drawings.

DESCRIPTION OF THE PREFERRED EMBODIMENTS

Figure 3:
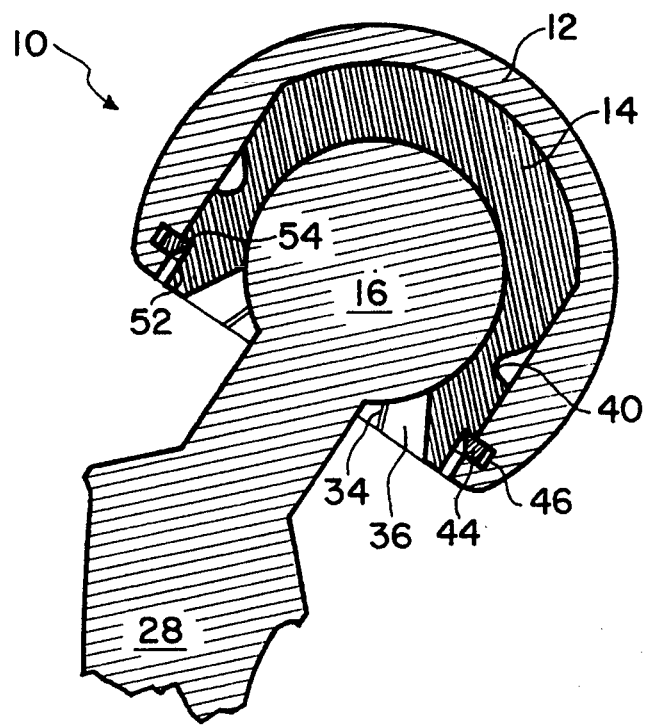
FIG. 3 is a partial longitudinal cross sectional view similar to FIG. 2 but with the implant in a fully assembled condition.
Figure 1:
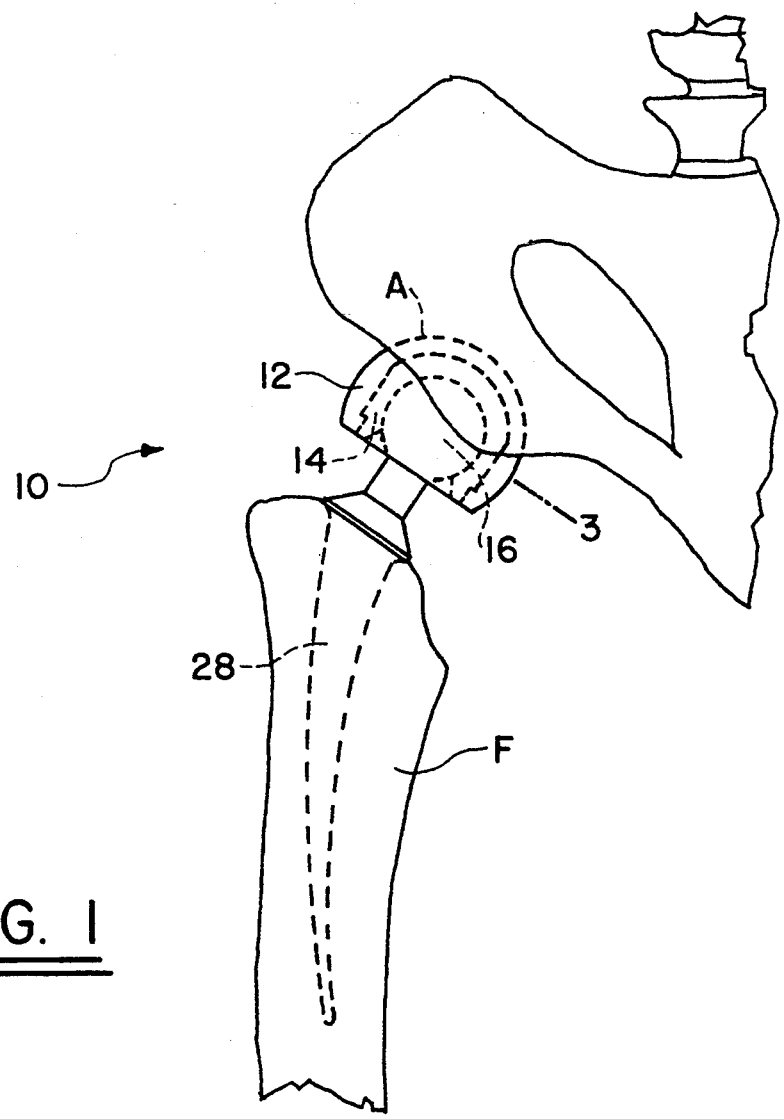
FIG. 1 is a partial perspective view illustrating a prosthetic implant embodying the principles of the invention applied to a hip joint.
Figure 2:
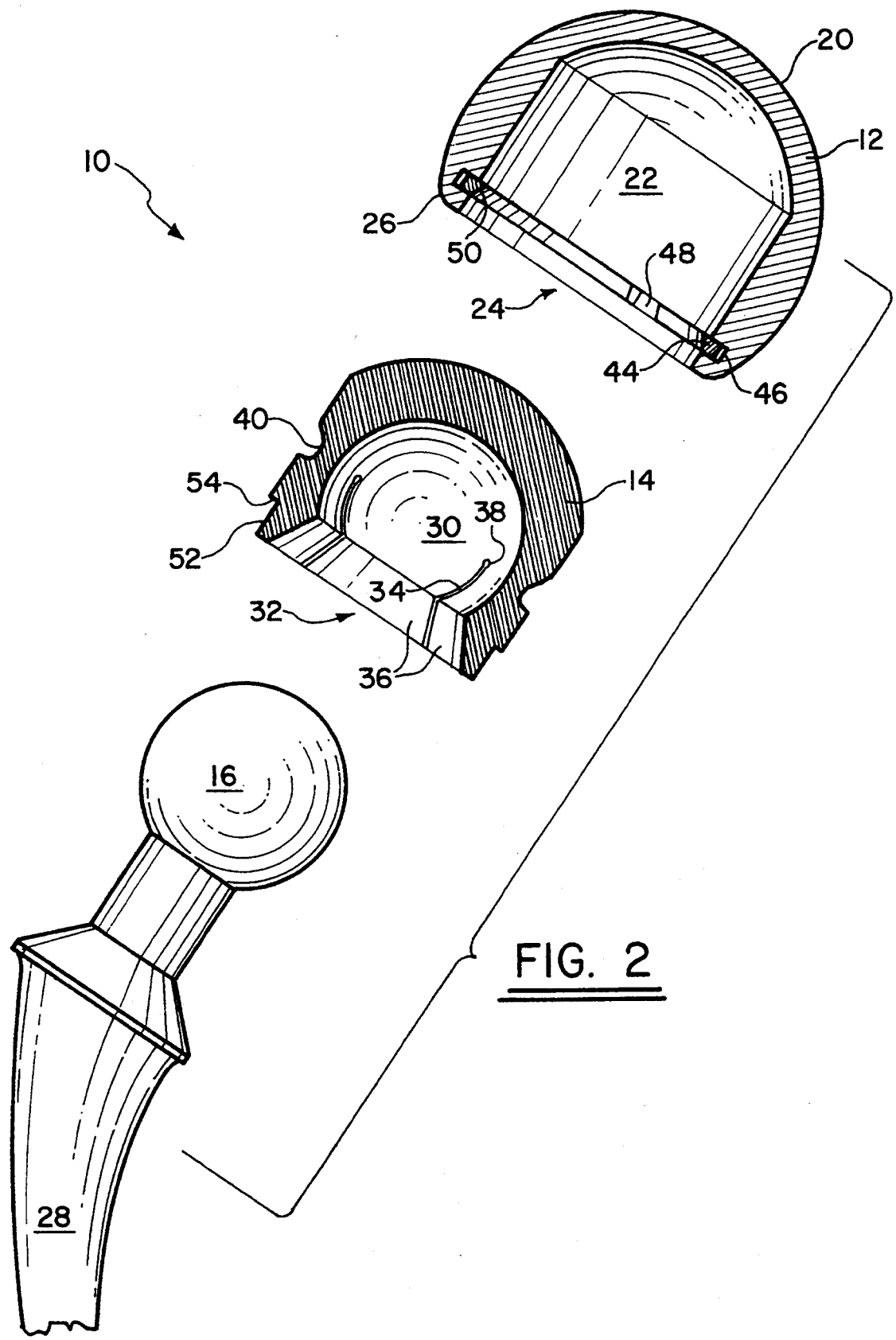
FIG. 2 is an isolated partial longitudinal cross sectional view of the implant in FIG. 1 in a partially unassembled condition.

FIGS. 1 through 3 illustrate the preferred form of prosthetic implant 10 embodying the principles of the invention. As best shown in FIG. 1, the implant 10 is adapted particularly for replacing an anatomical hip joint. The terminology used in the following description will therefore refer particularly to the anatomical structure in and around the hip joint. However, those skilled in the art will readily appreciate that a prosthetic implant embodying the principles of the invention may be used in other ball and socket type joint structures such as the shoulder joint for example.

The illustrated form of the invention includes a shell 12, an insert member 14, and an implant head or ball 16. The implant head 16 is adapted to be connected to the top of the femur F by suitable means as shown in FIG. 1 and is also adapted to be received in the insert member 14. The insert member 14 with the implant head 16 received therein is adapted to be received in the shell 12 and the shell is placed in the hip socket or acetabulum A and is held in place by tendons and ligaments (not shown).

The shell 12 is made from a biologically compatible material such as a cobalt-chromium-molybdenum alloy or titanium alloy and includes a substantially spherical outer bearing surface 20. The outer bearing surface 20 is highly polished to allow the shell to easily articulate in the acetabular socket A. An insert receptacle 22 is formed in the shell 12 with an insert receptacle opening 24 for receiving the insert member 14. The insert receptacle 22 has a generally cylindrical cross-sectional shape with a concave end opposite the end in which the insert receptacle opening 24 is formed. The shell 12 also includes a well rounded lower edge 26 to prevent abrasion of soft tissue adjacent to the implant 10 and to reduce the possibility of catching on any portion of the acetabulum A as the shell articulates therewith.

The head or ball 16 shown in FIGS. 2 and 3 is generally spherical in shape. A stem 28 is connected to the head 16 and is adapted to be received in the central canal of the femur F as shown in FIG. 1 to secure the head to the femur. The head 16 and stem 28 may be modular or integrally formed as shown in the figures and are both made of a suitable biologically compatible material similar to the shell 12. As with the shell 12 the head 16 is highly polished to minimize friction as it articulates with the insert member 14.

The insert member 14 is adapted to fit within the insert receptacle 22 of the shell 12 with minimum tolerance and therefore preferably has an outer shape that conforms to the shape of the insert receptacle 22. In the illustrated form of the invention, the insert member 14 has a generally cylindrical outer cross-sectional shape with a convex end adapted to abut the concave surface within the insert receptacle 22 when the insert member is in the fully received position shown in FIG. 3. A head receptacle 30 with a receptacle opening 32 thereto is formed in the insert member 14 for receiving the head 16. The head receptacle surface forms a bearing surface for the head 16 and is therefore preferably spherical in shape to match the shape of the head. Since the insert member 14 forms a bearing surface for the head 16 and is preferably resilient as discussed below, the preferred insert member is made of ultra high molecular weight polyethylene (UHMWPE).

At the end of the insert member 14 in which the head receptacle opening 32 is located, a series of radial slots 34 are spaced out at different angular orientations about the center longitudinal axis of the insert member forming a series of arms 36 there between. The slots 34 extend approximately one-half of the longitudinal dimension of the insert member 14 and each slot ends in an enlarged stress relief opening 38. A circumferential groove 40 is formed on the outer surface of the insert member 14 at a position generally coinciding with the ends of the slots 34. The groove 40 creates a reduced cross-section area at the base of each arm 36 and this reduced cross-section area allows the arms to flex outwardly to accept the head 16 in the head receptacle 30. The resiliency of the material from which the insert member 14 is formed causes the arms to return to a relaxed position once the head 16 is fully received in the head receptacle 30 and retain the head therein.

The prosthetic implant 10 according to the invention also includes locking means for locking the insert member 14 and head 16 received therein in the shell insert receptacle 22. The locking means in this form of the invention comprises a locking ring 44 adapted to fit in an annular groove or shell locking feature 46 formed on the wall of the shell insert receptacle 22 as shown in FIGS. 2 and 3. The locking ring 44 includes an opening 48 along a portion of its circumference and is made of a resilient material such as UHMWPE similar to the insert member 14. The resiliency of the material and the opening or split 48 allows the locking ring 44 to collapse to a decreased diameter and to expand to an increased diameter and in each case to return to a relaxed position and diameter. Also, the preferred locking ring 44 includes a bevel on its inside surface 50. When the locking ring 44 is properly positioned in the groove 46, the bevel surface 50 forms a frustoconical shape with the larger diameter end of the shape facing toward the insert receptacle opening 24 of the shell 12.

Referring particularly to FIG. 2, the locking ring 44 extends into the insert receptacle 22 when in a relaxed condition in the annular groove 46. When the insert member 14 with the head 16 received therein is inserted into the shell insert receptacle 22 through the insert receptacle opening 24, contact between the insert member and the locking ring 44 expands the ring and causes the ring to retract substantially from the insert receptacle. When the insert member 14 reaches a fully received position in the shell in which the longitudinal axes of the insert receptacle and the head receptacle are generally aligned, as shown in FIG. 3, a reduced diameter section 52 of the insert member aligns with the annular groove 46 and locking ring 44. This reduced diameter feature 52 on the insert member 14 allows the ring 44 to extend back to its relaxed shape and extend into the insert receptacle 22 to contact a step or insert member locking feature 54 formed by the reduced diameter section 52 on the insert member. This contact with the step 54 on the insert member 14 provides a positive lock to maintain the insert member in the fully received position.

Once in the fully received and locked position, the insert member 14 and head 16 can be removed only by expanding the ring 44 to again retract the ring from the insert receptacle 22 sufficiently to clear the step 54. Expanding the ring 44 can be accomplished easily by inserting a tool (not shown) into the annulus formed between the reduced diameter section 52 of the insert member 14 and the wall of the insert receptacle 22 in a direction substantially parallel to the longitudinal axis of the insert receptacle to contact the beveled surface 50 on the locking ring. Contact on the beveled surface 50 of the locking ring 44 applies an outward force component to expand the ring past the step 54 or other feature at which point the insert member 14 and head 16 received therein may freely slide out of the shell insert receptacle 22.

The prosthetic implant 10 embodying the principles of the invention has a number of advantages over prior implants for ball and socket type joints. First, when the insert member 14 is received in the fully received position shown in FIG. 3, the arms 36 on the insert member are constrained by the shell and can not flex outwardly. Thus the head 16 is securely locked in place but is free to articulate with the insert member 14. Thus the connection between the implant components is very strong yet the implant 10 can be disassembled easily simply by expanding the locking ring 44 as described above. Also, the locking mechanism does not interfere with the connection between the head 16 and insert member 14 and allows the insert member to provide a maximum bearing surface area for the head. Additionally, since the insert member 14 does not have to change outer cross-sectional shape to perform any locking function, the insert member may be designed with minimal tolerance with the insert receptacle 22 of the shell 12 and with the head 16. Furthermore, the implant 10 and locking mechanism comprises minimal parts and is easily and quickly assembled and disassembled during the surgical implantation procedure.

Pursuant to the method of assembling the prosthetic implant 10 according to the invention, the head 16 is first inserted into the head receptacle 30 in the insert member 14. With the head 16 received and retained in the insert member 14, the insert member is then pushed into the shell insert receptacle 22 through the insert receptacle opening 24. The method continues with the step of retracting the locking means, in the illustrated case the locking ring 44, substantially from the insert receptacle 22 to allow the insert member 14 to pass further into the insert receptacle. Once the insert member 14 is in the fully received position in the shell 12, the method includes extending the locking member 44 back into the insert receptacle 22 to contact the step 54 formed on the insert member thereby providing a positive lock to retain the insert member in the shell 12.

In the preferred form of the invention shown in the figures, the method also includes the step of continuously biasing the locking ring 44 to the relaxed position extending into the insert receptacle 22. The preferred method also includes maintaining the outer cross-sectional shape of the insert member 14 constant as the insert member is inserted into the shell receptacle 22. Maintaining a constant outer cross-sectional shape in the insert member 14 reduces the possibility of play between the insert member and head 16.

The above described preferred embodiments are intended to illustrate the principles of the invention, but not to limit the scope of the invention. Various other embodiments and modifications to these preferred embodiments may be made by those skilled in the art without departing from the scope of the following claims. For example, the insert, locking ring, and shell may be made of any suitable material. Also, the locking means need not be a split ring nor be continuously biased inwardly toward the insert receptacle 22. The locking means could alternatively be a member mounted on the shell 12 in position to be manually extended and retracted into and from the shell receptacle 22 to provide the locking function. Also, the locking means could be associated with the insert member rather than the shell. Furthermore, although the illustrated insert with resilient arms 36 is preferred for its ease of manufacture and one-piece design, any suitable structure may be used to retain the head 16 in and insert member.

We claim:

1. A prosthetic implant for joint structures, the implant comprising:
 (a) a shell having an insert receptacle with an insert receptacle opening thereto and a longitudinal insert receptacle axis;
 (b) an insert member having a head receptacle and head receptacle opening adapted for receiving a head member associated with the implant, the insert member being adapted to be received in a received position in the insert receptacle of the shell wherein the head receptacle opening is substantially aligned with the insert receptacle opening and the longitudinal insert receptacle axis is substantially aligned with a longitudinal head receptacle axis;

(c) a locking ring positioned around a circumference of the insert receptacle transverse to the longitudinal insert receptacle axis, the locking ring for extending between and contacting an insert member locking feature on the insert member and a shell locking feature on the shell when in a locked position with the insert member in the received position in the insert receptacle, thereby retaining the insert member in the received position in the shell, the locking ring also being capable of resiliently moving to a retracted position in which it does not simultaneously contact the insert member locking feature and the shell locking feature thereby enabling the insert member to be removed from the shell; and (d) a beveled surface formed on the locking ring and extending at an acute angle with respect to the longitudinal insert receptacle axis when the locking ring is in the locked position and the insert member is in the received position in the shell, the beveled surface for moving the locking ring from said locked position to the retracted position in response to a retracting force applied to the beveled surface in a direction substantially parallel to the longitudinal insert receptacle axis.

2. The implant of claim 1 wherein:

(a) the head receptacle of the insert member includes a head bearing surface that comprises a portion of a sphere greater than a hemisphere.

3. In a joint structure prosthetic implant including a shell having an insert receptacle with an insert receptacle opening thereto and a longitudinal insert receptacle axis, a substantially spherical head adapted to be secured to a bone leading to a joint in which the implant is to be used, and an insert member having a head receptacle and a head receptacle opening thereto for receiving the head and providing a bearing surface therefore, and wherein the insert member is adapted to be received in a received position in the insert receptacle of the shell through the insert receptacle opening so that the head receptacle opening is generally aligned with the insert receptacle opening, the improvement comprising:

(a) a locking ring positioned around a circumference of the insert receptacle transverse to the longitudinal insert receptacle axis, the locking ring for extending between and contacting an insert member locking feature on the insert member and a shell locking feature on the shell when in a locked position with the insert member in the received position in the insert receptacle, thereby retaining the insert member in the received position in the shell, the locking ring also being capable of resiliently moving to a retracted position in which it does not simultaneously contact the insert member locking feature and the shell locking feature thereby enabling the insert member to be removed from the shell; and (b) a beveled surface formed on the locking ring and extending at an acute angle with respect to the longitudinal insert receptacle axis when the locking ring is in the locked position and the insert member is in the received position in the shell, the beveled surface for moving the locking ring from said locked position to the retracted position in response to a retracting force applied to the beveled surface in a direction substantially parallel to the longitudinal insert receptacle axis.

4. The implant of claim 1 wherein the locking ring comprises:

(a) a ring of resilient material having an opening along part of its circumference for enabling the ring to expand and collapse, the ring being received in an inwardly directed annular groove formed in the shell.

5. The implant of claim 4 wherein:

(a) the ring includes an inside edge adapted to contact a circumferential step on the insert member when the ring is in the locked position and the insert member is in the received position in the shell insert receptacle.

6. The implant of claim 5 wherein:

(a) the beveled surface on the locking ring forms a substantially frustoconical shape with a larger diameter end of the shape facing toward the insert receptacle opening of the shell.

7. The implant of claim 1 wherein:

(a) the insert member has an outer transverse cross-sectional size and shape that remains substantially constant as the insert member is inserted into the insert receptacle of the shell.

8. The implant of claim 2 wherein the insert member includes:

(a) a series of longitudinally extending arms spaced out around its periphery at an end of the insert member in which the head receptacle opening is formed, the arms being adapted to bend outwardly to increase the size of the head receptacle opening sufficiently to allow the head member to be inserted therethrough and then resiliently bend back inwardly to retain the head member in the head receptacle.

9. The implant of claim 3 wherein the locking ring comprises:

(a) a ring of resilient material having an opening along part of its circumference for enabling the ring to expand and collapse, the ring being received in an inwardly directed annular groove formed in the shell.

10. The implant of claim 9 wherein:

(a) the ring includes an inside edge adapted to contact the insert member locking feature when the insert member is in the received position in the insert receptacle of the shell and the ring is in the locked position.

11. The implant of claim 10 wherein:

(a) the beveled surface on the locking ring forms a substantially frustoconical shape with a larger diameter end of the frustoconical shape facing toward the insert receptacle opening of the shell.

12. The implant of claim 3 wherein:

(a) the insert member has an outer transverse cross-sectional size and shape that remains substantially constant as the insert member is inserted into the insert receptacle of the shell.

* * * * *